United States Patent
Bristow

(10) Patent No.: US 9,622,473 B2
(45) Date of Patent: Apr. 18, 2017

(54) HERBICIDAL COMPOSITIONS

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

(*) Notice: Subject to any disclaimer, the term of this patent is extended or adjusted under 35 U.S.C. 154(b) by 0 days.

(21) Appl. No.: 15/179,046

(22) Filed: Jun. 10, 2016

(65) Prior Publication Data

US 2016/0278378 A1    Sep. 29, 2016

Related U.S. Application Data

(62) Division of application No. 13/817,327, filed as application No. PCT/CN2011/078475 on Aug. 16, 2011, now Pat. No. 9,386,768.

(30) Foreign Application Priority Data

Aug. 17, 2010   (GB) .................................. 1013799.0

(51) Int. Cl.
    *A01N 43/30*    (2006.01)
    *A01N 25/28*    (2006.01)
    *A01N 43/40*    (2006.01)

(52) U.S. Cl.
    CPC ............. *A01N 43/40* (2013.01); *A01N 25/28* (2013.01)

(58) Field of Classification Search
    CPC ........ A01N 43/40; A01N 25/02; A01N 25/28; C12N 2500/50
    See application file for complete search history.

(56) References Cited

FOREIGN PATENT DOCUMENTS

| CN | 101703069 A | | 5/2010 | |
|---|---|---|---|---|
| EP | 0 381290 | * | 1/1990 | ............. A01N 25/12 |
| EP | 1844653 | * | 10/2007 | ............. A01N 25/30 |
| IL | WO 03/075657 | * | 9/2003 | ............. A01N 25/04 |

OTHER PUBLICATIONS

Liu et al., "Application of Rosin as Encapsulation Material," College of Biological and Chemical Engineering, Kunming University of Science and Technology, Kunming 650224, China; Chemistry and Industry of Forest Products, vol. 23, No. 2, Jun. 2003.

* cited by examiner

*Primary Examiner* — Anna Falkowitz
(74) *Attorney, Agent, or Firm* — Dickinson Wright PLLC

(57) ABSTRACT

A herbicidal composition comprising an aqueous suspension of microcapsules, having a capsule wall of a porous condensate polymer, and containing a solution of fluoroxypyr in a rosin solvent system is provided. A herbicidal composition comprising microcapsules, having a capsule wall of a porous condensate polymer, and containing fluoroxypyr and a solvent comprising rosin and/or a rosin derivative, is also provided. A method of preparing a herbicidal composition is also disclosed, comprising providing a water immiscible phase comprising fluoroxypyr and an isocyanate dissolved in a rosin solvent system comprising rosin and/or a rosin derivative; providing an aqueous phase comprising one or more surfactants; combining the water immiscible phase and the aqueous phase to form a dispersion of the water immiscible phase in the aqueous phase; adding to the resulting dispersion an amine, thereby forming microcapsules of polyurea containing droplets of the water immiscible phase; and curing the microcapsules.

11 Claims, No Drawings

HERBICIDAL COMPOSITIONS

CROSS-REFERENCE TO RELATED APPLICATIONS

This application is a divisional of U.S. patent application Ser. No. 13/817,327 filed on Mar. 19, 2013, which claims the benefit and priority of PCT/CN2011/078475, filed Aug. 16, 2011 and GB 1013799.0, filed Aug. 17, 2010. The entire disclosures of each of the above applications are incorporated herein by reference.

The present invention relates to herbicidal compositions and their use. The present invention is particularly concerned with the provision of compositions of pyridinoxy acid herbicides, especially fluoroxypyr, and to use of the same in controlling unwanted plant growth.

Fluoroxypyr is a pyridinoxy acid herbicide used to control annual and perennial broad leaf weeds and woody brush. Formulations of fluoroxypyr are known and are available commercially. One commercial formulation of fluoroxypyr is a solvent-based emusifiable concentrate (EC). The formulation is typically prepared by dissolving the fluoroxypyr active ingredient in an inert organic liquid solvent, together with are appropriate emulsifier system. Mixing the resulting combination with water, spontaneously forms an oil in water emulsion of the fluoroxypyr/solvent solution.

Modern agricultural practice requires improved control in the application of biologically active components to the target plants. This improved control in turn provides for a number of advantages. First, the improved control of the active ingredient allows compounds to be used that have an increased stability over extended periods of time. Further, the improved control leads to a reduction in the environmental hazard presented by the herbicidal composition. In addition, improved control leads to a decrease in the acute toxicity of the composition and allows any incompatibility between ingredients to be accommodated.

It is known that microencapsulation is a technique that offers a number of advantages in improving the control achievable in the delivery of herbicidal formulations, compared with other formulation techniques in the field of agrochemicals. Several basic processes for the preparation of microencapsulation formulations of herbicidally active compounds have been disclosed and are known in the art. In particular, known techniques for microencapsulation include coacervation, interfacial polymerization and in-situ polymerization. Most commercially available CS (microcapsule suspension) formulations are manufactured by interfacial polymerization. Examples of commercial CS formulations prepared in this manner include Chlorpyrifos CS, Lambda-cyhalothrin CS, Clomazone CS, Fluorochloridone CS, and Methylparation CS. When such formulations are dried, they form water dispersible granules containing microcapsules, with the active ingredient being contained within the microcapsules. The microcapsules act to contain the active ingredient, such that when the formulation is applied, for example as a dispersion in water, the active ingredient is released slowly from the microcapsules and its spread outside the locus of application is limited.

Currently, while a significant number of active ingredients, such as those mentioned above, have been formulated using microencapsulation, it is not known to form formulations of fluoroxypyr in this way.

EP 1 844 653 suggests a water dispersible granule (WG) formulation of microencapsulated fluoroxypyr. The disclosure suggests using the known method of microencapsulation applied in the preparation of WG formulations of chlorpyrifos. However, the process yielded a formulation with an unsatisfactory distribution of the active ingredients. In the disclosed examples, a product was obtained having a wet sieving residue of more than 10%, of which 50% comprised crystallized fluoroxypyr present outside of the microcapsules.

One known method of preparing a CS formulation is by interfacial polymerization. In this method, the active ingredient is dissolved in a solvent, together with monomers and/or prepolymers. The resulting mixture is dispersed into a water phase containing one or more emulsifiers, optionally one or more protective colloids and, optionally, additional prepolymers. A capsule wall is formed around the oil droplets as a result of interfacial polymerization occurring at the oil/water interface in the presence of a catalyst or by heat.

Solvents, although generally inert in the finished formulation, are used in the microencapsulation of active ingredients to perform a number of roles, for example dissolving the active component to allow encapsulation of solid active ingredients, and adjusting the diffusion rate of the active substance through the polymeric wall, in turn aiding in controlling the release of the active ingredients from the microcapsules when the formulation has been applied. In addition, solvents may be selected, in addition to their role of dissolving the active components, to influence the emulsion quality, for example by maintaining a low viscosity during the emulsification and/or polymerization steps.

EP 1 652 433 describes a herbicidal formulation comprising an aqueous liquid composition having suspended therein a multitude of solid microcapsules, the microcapsules having a capsule wall of porous condensate polymer of at least one of a polyurea, polyamide or amide-urea copolymer. The microcapsules are formed to encapsulate clomazone as the active ingredient, wherein the clomazone is dissolved in a high boiling inert organic solvent, in particular a 1,2-benzenedicarboxylic di(C6-C3) branched alkyl ester.

EP 0 792 100 describes a process for preparing an encapsulated clomazone formulation. The process involves a step of providing a water immiscible liquid phase consisting of clomazone and polymethylene polyphenyl isocyanate, with or without an aromatic hydrocarbon solvent. EP 0 792 100 describes the microencapsulation of clomazone by preparing a water-immiscible phase containing specified amounts of clomazone and polymethylene polyphenyl isocyanate (PMPPI), together with an aromatic solvent. The solvent is indicated to be optional in the case of formulations with high loadings of clomazone. However, the exemplified formulations generally contain a petroleum solvent in an amount of from 4 to 6% by weight.

It would be advantageous if fluoroxypyr could be formulated using microencapsulation techniques, for example in a similar manner to the known microencapsulated clomazone formulations. However, as noted above, attempts to microencapsulate fluoroxypyr have not been fully successful. There is therefore a need for an improved formulation of fluoroxypyr, in particular a formulation based on microencapsulation of the active ingredient.

Surprisingly, it has been found that effective microencapsulated formulations of fluoroxypyr may be prepared using rosin and/or rosin derivatives as solvents. In particular, it has been found that the use of rosin and/or rosin derivatives provides the fluoroxypyr with a high dispersability, while still allowing the formulation to be readily suspended in water. Further, the formulation exhibits a low wet sieve residue that is a high degree of retention of the fluoroxypyr active ingredient in the microcapsules. It has also been found that the rosin and/or rosin derivatives exhibit a lower toxicity than solvents used in the prior art formulations, in particular the 1,2-benzenedicarboxylic di($C_3$-$C_6$) branched alkyl esters and the aromatic hydrocarbon and petroleum solvents described above.

Accordingly, in a first aspect, the present invention provides a herbicidal composition comprising an aqueous suspension of microcapsules, the microcapsules having a capsule wall of a porous condensate polymer, wherein the microcapsules contain a solution of fluoroxypyr in a rosin solvent system comprising rosin and/or a rosin derivative.

Surprisingly, it has been found that microencapsulating fluoroxypyr in a solvent comprising rosin and/or a rosin derivative provides a significantly improved formulation, in particular having the properties of a high dispersibility, ease of forming and maintaining in suspension, and a low wet sieve residue. A further advantage is that the rosin and rosin derivatives used as solvents for the fluoroxypyr are significantly less toxic than the solvents known and used in the prior art formulations.

The fluoroxypyr formulation of the present invention comprises microcapsules suspended in an aqueous phase. The microcapsules contain a solution of fluoroxypyr in a solvent phase comprising rosin and/or a rosin derivative, such that the fluoroxypyr in the formulation is retained within the microcapsules.

Fluroxypyr is the common name of 4-amino-3,5-dichloro-6-fluoro-2-pyridyloxyacetic acid, a compound known to be herbicidally active and commercially available. The formulation of the present invention may comprise fluoroxypyr as the sole herbicidally active ingredient. Alternatively, one or more further active ingredients may be present in the formulation, either within the microcapsules and/or within the aqueous phase.

The formulation may comprise fluoroxypyr in any suitable amount to provide the required level of activity, when applied to a locus for the control of plant growth. Preferably, the formulation contains fluoroxypyr in an amount of at least 10% by weight, more preferably at least 20%, still more preferably at least 40%. Formulations having at least 50% by weight fluoroxypyr are also envisaged in the present invention.

In the formulation of the present invention, fluoroxypyr is retained in solution in an organic solvent system within the microcapsules. The solvent comprises rosin and/or a rosin derivative. Other solvents may be present within the microcapsules. However, it is preferred that the solvent consists essentially of rosin and/or one or more rosin derivatives. Rosin and its derivatives are insoluble in water. Rosin and its derivatives are known in the art and are commercially available. Rosin derivatives that may be used as or included in the solvent system of the formulation include any derivative that is a liquid under ambient conditions and in which fluoroxypyr is soluble. Suitable derivatives include hydrogenated rosin, polymerized rosin, esters of rosin or hydrogenated rosin, in particular methyl esters of rosin or of hydrogenated rosin, glycerol esters of rosin or hydrogenated rosin, triethylene glycol esters of rosin or hydrogenated rosin and pentaerythratol esters of rosin or hydrogenated rosin.

The microcapsules may contain a solution consisting essentially of rosin and/or a rosin ester and fluorxypyr. Other components may be included in the solvent system, as required. Other components that may be present in the solution are known in the art and include surfactants, stabilizers and the like. In particular, antioxidants may be included in the solvent system within the microcapsules. As described in more detail below, preparation of the formulation may require heating of the formulation to cure the polymers walls of the microcapsules. Heating the formulation may increase the rate of oxidation of the active components. Accordingly, one or more antioxidants may be included. Suitable antioxidants are known in the art and are commercially available. Examples include butylated hydroxytoluene (BHT) and butylated hydroxyanisole (BHA). The antioxidant may be present in any suitable amount to reduce or prevent oxidation of the active ingredient and maintain its stability. The amount of antioxidant may be in the range of from 0.005 to 1.0% of the weight of the microcapsules, more preferably from 0.01 to 0.05% by weight.

The size of the microcapsules may controlled by a number of factors in the preparation of the composition of this invention. In particular, the size of the microcapsules may be controlled by including on or more further components in the water-immiscible liquid phase within the microcapsules, in particular one or more surfactants. The hydrophile-lipophile balance (HLB) of the surfactants employed can influence the size of the microcapsules formed in the composition, with surfactants or surfactant combinations having a lower HLB giving use to microcapsules having a lower diameter. Suitable oil-soluble surfactants are known and available commercially, for example Atlox 4912, an A-B-A block copolymer surfactant having a low HLB of about 5.5. Other block copolymer surfactants may be used, in particular those composed of polyglycol, for example polypropylenglycol, and hydroxylated polyfatty acids. The surfactants may be present in any suitable amount to impart the required particle size to the microcapsules during preparing of the composition. A preferred concentration in the water-immiscible phase is from 1 to 30%, more preferably about 5 to 25% by weight of the microcapsules.

The rosin-based solvent system within the microcapsules may further comprise one or more oil-soluble cross-linking agents. Suitable cross-linking agents include carbamides, such as acetylene carbamide and derivatives thereof, fats or resins, such as the copolymerization product of styrene and maleic anhydride. Such cross-linking agents are known in the art and are commercially available, for example Powder Link 1174 (1,3,4,6-tetrakis(methoxymethyl)glycoluril). The cross-linking agent and the amount present may be used to control the porosity of the polymer wall of the microcapsules. Preferably, the composition comprises the cross-linking agent in an amount of from 0.1 to 20%, more preferably from 0.5 to 15% by weight of the microcapsules.

The rosin solvent system within the microcapsules contains the solvent, in particular the rosin and/or rosin derivatives, in sufficient amount to dissolve the required amount of fluoroxypyr. Preferably, the weight ratio of fluoroxypyr to rosin solvent is from 1:10 to 10:1, more preferably from 1:5 to 5:1, still more preferably from 2:5 to 5:2.

The liquid phase within the microcapsules preferably contains at least 20% by weight fluoroxypyr, more preferably at least 30%, still more preferably at least 50% by weight fluoroxypyr. Fluoroxypyr may be present in the encapsulated material in an amount of from 1% to 95% by weight, more preferably from 1% to 90%, still more preferably from 5% to 90% by weight.

The rosin and/or rosin derivative solvent is preferably present in the liquid within the microcapsules in an amount of at least 10% by weight, more preferably at least 20% by weight, still more preferably at least 30% by weight.

The solution of fluoroxypyr in the rosin solvent system is contained within the microcapsules. The microcapsules may be formed from any suitable polymer. The polymer of the microcapsules is porous, thereby allowing for the controlled release of the fluoroxypyr active ingredient from within the microcapsules. The rate of release of the active ingredient from the microcapsules may be controlled in known manner, for example by the appropriate selection of the polymers used to prepare the microcapsules, selection of the size of the microcapsules, the porosity of the polymer, and the presence of components within the microcapsules. Suitable polymer systems for use in the microencapsulation formulation of the present invention are known in the art. The polymer forming the wall of the microcapsules is preferably formed by interfacial polymerization. Examples of suitable polymers to form the microcapsules include porous condensate polymers of one or more of a polyurea, polyamide or amide-urea copolymer.

Polyureas are preferred polymers for the microcapsules. Polyureas may be formed by the interfacial polymerization of an isocyanate, in particular a polyfunctional isocyanate, with an amine. Suitable isocyanates for forming the polyureas are known in the art and are commercially available, including polymethylene polyphenyl isocyanates (PMPPI), methylene diphenyl isocyanate (MDI), polymeric methylene diphenyl isocyanate (PADI), and toluene diisocyanate (TDI). The amine may be a mono- or polyfunctional amine. Suitable amines for forming the polymeric wall of the microcapsules are known and the art and are commercially available, including ethylenediamine (EDA), diethyltriamine (DETA), triethylenetetramine (TETA), 1,6-hexamine (HAD), and triethyleamine (TEA).

As noted above, the size of the microcapsules may be selected to provide the required properties of the formulation, in particular the rate of release of the fluoroxypyr active ingredient from the microcapsules. The microcapsules may have a particle size in the range of from 0.5 to 60 microns, more preferably from 1 to 60 microns, still more preferably from 1 to 50 microns. A particle size range of from 1 to 40 microns, more preferably from 1 to 30 microns has been found to be particularly suitable.

The microcapsules may comprise the polymer in a suitable amount to provide the required properties of the formulation. Preferably, the polymer is present in an amount of from 2% to 25% by weight of the microcapsules, more preferably from 3 to 20%, still more preferably from 5 to 15% by weight. A particularly suitable amount of polymer in the microcapsules is in the range of from 5 to 12% by weight.

The formulation of the first aspect of the present invention comprises the microcapsules as described above suspended in an aqueous phase. The aqueous phase comprises water, together with other components required to impart the desired properties to the formulation, for example stability of the suspension and dispersibility of the microcapsules. Suitable components for inclusion in the aqueous phase of the formulation are known in the art and are commercially available. Suitable components are those that improve and maintain the dispersibility and suspension of the microcapsules, and include one or more surfactants, stabilizers, emulsifiers, viscosity modifiers, protective colloids, and the like.

The aqueous phase may make up any suitable amount of the formulation, provided the microcapsules are well dispersed and maintained in suspension. Typically, the aqueous phase will comprise from 15 to 50% by weight of the formulation, more preferably from 20 to 40%, still more preferably from 25 to 30%.

The formulation of the present invention may be used in known manner to control the growth of plants. In particular, the formulation may be diluted with water to the required concentration of active ingredient and applied to a locus in known manner, such as by spraying.

It has also been found that the formulation of the present invention may be prepared in a dried form that is without the microcapsules being suspended in an aqueous phase. Accordingly, in a further aspect, the present invention provides a herbicidal composition comprising microcapsules, the microcapsules having a capsule wall of a porous condensate polymer, wherein the microcapsules contain fluoroxypyr and a solvent comprising rosin and/or a rosin derivative.

Details of the microcapsules and their composition are as hereinbefore described.

The formulation of this aspect of the invention, in use, is typically mixed with water to the required level of dilution to form a suspension of microcapsules in an aqueous phase, which may then be used and applied in known manner, as described above.

The formulations of the present invention may be prepared in a manner analogous to the preparation of known microencapsulation formulations. In general, the reactants forming the polymer of the walls of the microcapsules are dispersed between an organic liquid phase and an aqueous liquid phase, such that polymerization takes place at the interface between the two phases. For example, in the case of microcapsules formed from polyurea, the isocyanate is dispersed in the organic rosin solvent system, together with the fluoroxypyr active ingredient, while the amine is dispersed in the aqueous phase. The two phases are then mixed, to allow the polymer to form at the interface.

In a further aspect, the present invention provides a method for preparing a herbicide composition, the method comprising the steps of:

providing a water immiscible phase comprising fluoroxypyr and an isocyanate dissolved in a rosin solvent system comprising rosin and/or a rosin derivative;

providing an aqueous phase comprising one or more surfactants;

combining the water immiscible phase and the aqueous phase to form a dispersion of the water immiscible phase in the aqueous phase;

adding to the resulting dispersion an amine, thereby forming microcapsules of polyurea containing droplets of the water immiscible phase; and curing the microcapsules.

The method comprises combining a water immiscible phase and an aqueous phase. This is carried out under conditions, such as with agitation, to form a dispersion of the water immiscible phase in the aqueous phase. The amine is preferably added to the resulting dispersion as an aqueous solution, thereby initiating the polymerization reaction.

The aqueous phase contains at least one surfactant or emulsifier, to assist in forming the dispersion of the water immiscible phase in the aqueous phase. Other components required to impart the desired properties to the final composition, as noted above, may be included in the aqueous phase.

The microcapsules are formed by interfacial polymerization reactions between the isocyanate and the amine. The polymerization reaction is preferably allowed to proceed while the dispersion is being agitated. The microcapsules once formed are cured, preferably by heating, to harden the polymer walls of the microcapsules. Curing typically takes place at a temperature of from 30 to 60° C., more preferably from 40 to 50° C., for a suitable length of time, typically from 1 to 5 hours, more typically from about 2 to 4 hours.

The resulting composition is preferably then filtered, after cooling, to provide a suspension of the microcapsules in the aqueous phase. The resulting product is a CS formulation of fluoroxypyr suitable for use and application as described above, in particular by dilution with water and application by spraying. Should it be required to prepare dry microcapsules, the resulting composition is subject to a drying stage, to remove the aqueous phase. Any suitable drying techniques may be employed, with spray drying being particularly effective.

The composition may be prepared with microcapsules formed from other polymers, as noted hereinbefore, using the appropriate wall-forming reagents in an analogous manner to the above procedure.

In a further aspect, the present invention provides the use of a fluoroxypyr formulation as hereinbefore described in the control of plant growth. In a still further aspect, the present invention provides a method of controlling plant growth at a locus, the method comprising applying to the locus a formulation of microencapsulated fluoroxypyr as hereinbefore described.

Embodiments of the present invention will now be described, for illustration only, by way of the following examples.

EXAMPLE 1

Preparation of a Formulation of Microencapsulated Fluoroxypyr

A water immiscible phase and an aqueous phase were prepared having the following composition (with amounts of the components expressed in weight of the final composition):

| Water Immiscible Phase | |
|---|---|
| Fluroxypyr | 50.0 |
| PAPI (ex. Dow Chemicals) | 3.50 |
| Methyl ester of hydrogenated rosin | 20.0 |
| Water Phase | |
| Atlox 4913 (surfactant ex. Croda International) | 0.6 |
| Citric acid | 0.14 |
| Triethyl amine (catalyst, 20% emulsion) | 0.25 |
| Water | 25.51 |

The PAPI, fluoroxypyr and rosin derivative were combined with stirring to form a uniform water immiscible liquid mixture. A solution of Atlox 4913 in water was heated in a Warning blender cup to about 50° C. The solution was agitated while the water immiscible liquid mixture was slowly added, to form a uniform emulsion of the water immiscible phase dispersed evenly throughout the continuous aqueous phase.

The aqueous solution of triethyl amine was added slowly, upon which interfacial polymerization occurred, producing microcapsules having a particle size of from 1 to 30 microns. Once the polymerization reaction had finished, the resulting composition was cured by heating to 50° C. for 2 hours. The resulting product was cooled and filtered, to obtain an agriculturally suitable CS formulation of microencapsulated fluoroxypyr.

The resultant product was tested for dispersibility and suspensibility of the microcapsules, and the wet sieve residue. It was found that the formulation had a suspensibility of greater than 90%, a dispersibility of greater than 90% and a wet sieve residue of less than 0.1%. The results show that the formulations of the present invention, by employing a rosin solvent system for the fluoroxypyr active ingredient, exhibit significantly improved properties compared with the prior art formulations.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the FIGURES. Spatially relative terms may be intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A method for preparing a herbicidal composition, the method comprising the steps of:
   providing a water immiscible phase comprising fluoroxypyr and an isocyanate dissolved in a rosin solvent system comprising methyl ester of hydrogenated rosin, the weight ratio of the fluoroxypyr to the rosin solvent being from 1:10 to 10:1;
   providing an aqueous phase comprising one or more surfactants;
   combining the water immiscible phase and the aqueous phase to form a dispersion of the water immiscible phase in the aqueous phase;
   adding to the resulting dispersion an amine, thereby forming microcapsules of polyurea, the polyurea being formed from polymethylene polyphenol isocyanate, and the microcapsules containing droplets of the water immiscible phase, wherein the fluoroxypyr is present in an amount of 50% by weight of the microcapsules, the polymer is present in an of amount 3.5% by weight of the microcapsules, and the methyl ester of hydrogenated rosin is present in an amount of 20% by weight of the microcapsules; and
   curing the microcapsules, wherein the microcapsules have a suspensibility of greater than 90%, a dispersibility of greater than 90%, and a wet sieve residue of less than 0.1%.

2. The method according to claim 1, further comprising drying the resulting composition to remove the aqueous phase.

3. The method according to claim 1, further comprising cooling and filtering the resultant mixture to provide a suspension of the microcapsules in the aqueous phase.

4. The method according to claim 1, wherein the rosin solvent system consists essentially of rosin and/or a rosin derivative.

5. The method according to claim 1, wherein the microcapsules contain one or more components selected from surfactants and stabilizers.

6. The method according to claim 1, wherein the walls of the microcapsules are formed from a polyurea formed by the interfacial polymerization of an isocyanate and an amine.

7. The method according to claim 6, wherein the amine is selected from the group consisting of ethylenediamine (EDA), diethyltriamine (DETA), triethylenetetramine (TETA), 1,6-hexamine (HAD), and triethyleamine (TEA).

8. The method according to claim 1, wherein the aqueous phase comprises one or more stabilizers, viscosity modifiers, or protective colloids.

9. The method according to claim 1, wherein the aqueous phase comprises from 15 to 50% by weight of the formulation.

10. The method according to claim 1, wherein the microcapsules contain surfactant in an amount of 0.6% by weight of the microcapsules, citric acid in an amount of 0.14% by weight of the microcapsules, catalyst in an amount of 0.25% by weight of the microcapsules, and water in an amount of 25.51% by weight of the microcapsules.

11. A method of controlling plant growth at a locus, the method comprising applying to the locus a composition prepared according to the method of claim 1.

* * * * *